(12) United States Patent
Anderheggen et al.

(10) Patent No.: US 9,789,053 B2
(45) Date of Patent: Oct. 17, 2017

(54) TRANSPARENT BLEACHING COMPOSITIONS WITH PROTEINS AND/OR SILICONE OILS

(71) Applicant: Henkel AG & Co. KGaA, Duesseldorf (DE)

(72) Inventors: Bernd Anderheggen, Moenchengladbach (DE); Frank Janssen, Cologne (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 14/937,997

(22) Filed: Nov. 11, 2015

(65) Prior Publication Data

US 2016/0058688 A1 Mar. 3, 2016

Related U.S. Application Data

(63) Continuation of application No. PCT/EP2014/052590, filed on Feb. 11, 2014.

(30) Foreign Application Priority Data

May 16, 2013 (DE) ........................ 10 2013 209 098

(51) Int. Cl.
| | |
|---|---|
| *A61Q 5/08* | (2006.01) |
| *A61K 8/891* | (2006.01) |
| *A61K 8/65* | (2006.01) |
| *A61K 8/22* | (2006.01) |
| *A61K 8/23* | (2006.01) |
| *A61K 8/73* | (2006.01) |
| *A61K 8/898* | (2006.01) |

(52) U.S. Cl.
CPC ............... *A61K 8/891* (2013.01); *A61K 8/22* (2013.01); *A61K 8/23* (2013.01); *A61K 8/65* (2013.01); *A61K 8/73* (2013.01); *A61K 8/898* (2013.01); *A61Q 5/08* (2013.01); *A61K 2800/262* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 7,534,272 B2 | 5/2009 | Cassier et al. | |
| 2006/0210499 A1 | 9/2006 | Hoeffkes et al. | |
| 2006/0254001 A1* | 11/2006 | Hoeffkes .................. | A61K 8/22 8/405 |
| 2011/0126361 A1 | 6/2011 | Manneck | |
| 2012/0315236 A1 | 12/2012 | Goutsis et al. | |

FOREIGN PATENT DOCUMENTS

| | | |
|---|---|---|
| DE | 10315421 A1 | 10/2004 |
| DE | 102004061468 A1 | 6/2006 |
| DE | 102006008149 A1 | 8/2007 |
| DE | 102007041490 A1 | 3/2009 |
| DE | 102010030337 A1 | 12/2011 |

OTHER PUBLICATIONS

PCT International Search Report (PCT/EP2014/052590) dated Jun. 23, 2014.

* cited by examiner

Primary Examiner — Jyothsna Venkat
(74) Attorney, Agent, or Firm — P. Scott Smith

(57) ABSTRACT

The present invention relates to agents for lightening keratinic fibers, comprising at least two preparations (A) and (B) packaged separately from each other, and optionally a further preparation (C) packaged separately from (A) and (B), which are mixed immediately before use to form an application mixture, wherein preparation (A) comprises at least one persulfate and preparation (B) is flowable and includes at least one oxidizing agent, and preparation (B) and/or preparations (C) moreover comprise at least one natural polymer, and preparation (A)—based on the weight thereof—comprises a1) 0 to 3 wt. % keratin hydrolysate(s) and/or a2) 0 to 5 wt. % silicone oil(s), with the proviso that preparation (A)—based on the weight thereof—comprises 0.1 to 6 wt. % compound(s) from the groups a1) and a2).

11 Claims, No Drawings

TRANSPARENT BLEACHING COMPOSITIONS WITH PROTEINS AND/OR SILICONE OILS

FIELD OF THE INVENTION

The present invention generally relates to agents for oxidatively changing a color in the cosmetics field, which are particularly suitable for lightening keratinic fibers, in particular human hair.

BACKGROUND OF THE INVENTION

The oxidizing agents present in blonding agents are capable of lightening the hair fiber by oxidatively destroying melanin, the hair's own pigment. For a moderate blonding effect, it is sufficient to use hydrogen peroxide—optionally with the use of ammonia or other alkalizing agents—as the only oxidizing agent; to achieve a stronger blonding effect, a mixture of hydrogen peroxide and peroxodisulfate salts and/or peroxomonosulfate salts is typically used.

For stability reasons, commercially available blonding agents are customarily offered in two preparations that are packaged separately from each other and mixed immediately before use to form a completely mixed application preparation. Commercially available blonding agents are usually composed of a liquid oxidizing agent preparation and a powder that includes solid oxidizing agents. Products comprising additional components are likewise offered commercially.

Monitoring the lightening process on the fiber is an important aspect in the use of blonding agents. The hairdresser usually checks the decolorizing process at least once during the exposure time. Commercially available blonding agents are generally white to colored, turbid gels or emulsions in the ready-to-use state. When using these blonding agents, it is necessary to remove the agent in one or multiple regions of the fibers during the exposure time to check the decolorizing process. The customer is thus able to assess the progress of the color change. If necessary, the application mixture can subsequently be re-applied to the corresponding locations on the fiber to continue the lightening process. The procedure may have to be repeated for further monitoring, if necessary. The use of transparent application mixtures considerably simplifies this monitoring step. It is not necessary to remove the blonding agent from the fiber. Instead, the transparency of the application mixture allows direct, visual assessment of the decoloring process at any point during the exposure time. The provision of transparent blonding agents consequently results in improved handling of the blonding agent and in simplified use.

DE 10 2007 041 490 A1 discloses blonding agents that allow the progress of the lightening process to be observed without labor-intensive steps and without the risk of impairing the blonding result.

WO 2005/067874 A1 describes blonding agents comprising a mixture composed of an oxidizing agent, at least one stabilizer, at least one polymer thickener made of synthetic polymers and alkali magnesium silicates, and water or an aqueous solvent. According to this invention, "transparency" and a "thickened consistency" are described as desirable properties of the agent.

DE 10 2010 042 252 A1 discloses agents for lightening keratinic fibers, comprising at least two preparations (A) and (B) packaged separately from each other, and optionally a further preparation (C) packaged separately from (A) and (B), which are mixed immediately before use to form an application mixture, wherein preparations (A) contain at least one persulfate and preparations (B) are flowable and contain at least one oxidizing agent, and wherein preparations (A) and/or preparations (C) moreover contain at least one natural polymer.

The oxidative treatment of keratinic fibers not only creates the desired lightening result, but also poses a burden on the fibers and, in the worst case, may damage the fiber structure. So as to minimize these negative effects, conventional, non-transparent blonding agents not according to the invention include care substances, which have repairing and conditioning effects. However, many of the customarily used care substances result in a considerable loss or in a considerable impairment of transparency in transparent blonding agents, which negates the advantage of using these agents. Other care substances weaken the blonding performance, so that use of the same is not indicated.

It was the object of the present invention to improve the properties of transparent blonding agents with respect to the care properties, without impairing the performance or the transparency of the same.

It has been shown that oxidizing agent preparations thickened with a natural polymer can be mixed with blonding powders to form a flowable preparation, which allows good homogenization of the two components to yield a ready-to-use application mixture. In this special matrix, certain proteins in combination with/without silicone oil result in permanent care effects, without impairing transparency. Moreover, the blonding performance is enhanced.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Agents for lightening keratinic fibers, comprising at least two preparations (A) and (B) packaged separately from each other, and optionally a further preparation (C) packaged separately from (A) and (B), which are mixed immediately before use to form an application mixture, wherein preparation (A) comprises at least one persulfate, and preparation (B) is flowable and includes at least one oxidizing agent, and preparation (B) and/or preparation (C) moreover contain at least one natural polymer, characterized in that preparation (A)—based on the weight thereof—comprises 0 to 3 wt. % keratin hydrolysate(s) and/or 0 to 5 wt. % silicone oil(s), with the proviso that preparation (A)—based on the weight thereof—comprises 0.1 to 6 wt. % compound(s) from groups a1) and a2).

A method for changing the color of keratinic fibers in which at least two preparations (A) and (B) packaged separately from each other, of which preparation (A) includes at least one persulfate and preparation (B) includes at least one oxidizing agent, are mixed to form an application mixture, this mixture is applied to the fibers and rinsed off again after an exposure time, characterized in that preparation (B) and/or an optionally present preparation (C) comprise at least one natural polymer, and preparation (A)—based on the weight thereof—comprises 0 to 3 wt. % keratin hydrolysate(s) and/or 0 to 5 wt. % silicone oil(s), with the proviso that preparation (A)—based on the weight thereof—comprises 0.1 to 6 wt. % compound(s) from groups a1) and a2).

Use of keratin hydrolysates and/or silicone oils to increase the lightening and care performance of transparent blonding agents.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In a first embodiment, the object of the present invention is agents for lightening keratinic fibers, comprising at least two preparations (A) and (B) packaged separately from each other, and optionally a further preparation (C) packaged separately from (A) and (B), which are mixed immediately before use to form an application mixture, wherein
 i. preparation (A) comprises at least one persulfate and
 ii. preparation (B) is flowable and includes at least one oxidizing agent,
 iii. preparation (B) and/or preparation (C) moreover includes or contain at least one natural polymer,
and preparation (A)—based on the weight thereof—includes
 a1) 0 to 3 wt. % keratin hydrolysate(s) and/or
 b2) 0 to 5 wt. % silicone oil(s),
with the proviso that preparation (A)—based on the weight thereof—comprises 0.1 to 6 wt. % compound(s) from groups a1) and a2).

Keratinic fibers, or also keratin fibers, shall be understood to mean furs, wool, feathers, and in particular human hair. Although the agents according to the invention are primarily suitable for lightening keratin fibers, in principle there are no objections to using them in other fields as well.

Preparations (A) are preferably powdery. It is possible to use powders made of solid components having different particle sizes. Typically it may be preferred, however, for the powders to have a substantially homogeneous particle size, in particular to simplify uniform dispersion or dissolution of the powders in preparations (B).

Preparations (A) may contain the active ingredients in a solid cosmetic carrier. A solid cosmetic carrier may contain silicic acid salts, in particular silicate and metasilicate salts with ammonium, alkali metals and alkaline earth metals. In particular the use of metasilicates may be preferred which according to formula $(SiO_2)_n(M_2O)_n$, where M denotes an ammonium ion, an alkali metal or a half stoichiometric equivalent of an alkaline earth metal, are characterized by the ratio of n to m of $\leq 1$ and can be considered chain-like polymeric structures of the anion $[SiO_3]^{2-}$. Sodium metasilicate of formula $[Na_2SiO_3]^\infty$ is particularly preferred. Likewise preferred according to the invention are silicates which are formed from a silicate of formula $(SiO_2)_n(Na_2O)_m (K_2O)_p$, where n denotes a positive rational number and m and p, independently of one another, denote a positive rational number or 0, with the proviso that at least one of the parameters m or p is different from 0 and the ratio of n to the sum of m and p is between 2:1 and 4:1.

Moreover, the solid cosmetic carriers may contain what are known as anti-caking agents, which are intended to prevent clumping or caking of the powder components. Preferably water-insoluble hydrophobing or moisture-adsorbing powders of diatomaceous earth, fumed silica, calcium phosphate, calcium silicates, aluminum oxide, magnesium oxide, magnesium carbonate, zinc oxide, stearates, fatty amines and the like may be used as such anti-caking agents. Finally, the solid cosmetic carriers may additionally contain an anti-dusting agent, which prevents dust formation of the powdery components. In particular inert oils may be used for this purpose. The solid cosmetic carriers preferably contain ester oils or mineral oils, preferably hydrocarbon oils, such as liquid paraffin oil, as the anti-dusting agent.

The first essential ingredient that preparation (A) comprises is at least one persulfate. Persulfates suitable according to the invention are inorganic peroxo compounds. These are preferably selected from ammonium peroxodisulfate, alkali metal peroxodisulfates, ammonium peroxomonosulfate, alkali metal peroxomonosulfates, alkali metal peroxodiphosphates and/or alkaline earth metal peroxides. Ammonium peroxodisulfate and/or alkali metal peroxodisulfates are particularly preferred.

In a preferred embodiment of the present invention, the persulfate that preparation (A) comprises is at least one peroxodisulfate salt, in particular selected from ammonium peroxodisulfate and/or potassium peroxodisulfate and/or sodium peroxodisulfate.

Moreover, it has proven to be particularly preferred while conducting the work of the present invention for preparations (A) to contain at least two different peroxodisulfates. Preferred peroxodisulfate salts are combinations of ammonium peroxodisulfate with potassium peroxodisulfate and/or sodium peroxodisulfate.

Preparations (A) especially contain persulfate salts in a quantity from 0.1 to 80 wt. %, preferably from 2 to 50 wt. %, particularly preferably from 3 to 30 wt. %, and more particularly preferably 5 to 15 wt. %, explicitly 5, 6, 7, 8, 9, 10, 11, 12, 13, 14 or 15 wt. %, in each case based on the total weight of the agent.

According to the invention, preparation (B) and/or preparation (C) moreover contain at least one natural polymer (see below). Preparation (A) is preferably free from xanthan since it has been found that this improves the lightening performance.

Preferred agents according to the invention are characterized in that preparation (A) is free from xanthan and—based on the weight of the preparation—includes 5 to 60 wt. %, preferably 10 to 55 wt. %, particularly preferably 1t to 50 wt. %, and in particular 20 to 45 wt. % of at least one persulfate, selected from ammonium peroxodisulfate and/or potassium peroxodisulfate and/or sodium peroxodisulfate.

According to the invention, preparation (A)—based on the weight thereof—includes
 a1) 0 to 3 wt. % keratin hydrolysate(s) and/or
 b2) 0 to 5 wt. % silicone oil(s),
with the proviso that preparation (A)—based on the weight thereof—comprises 0.1 to 6 wt. % compound(s) from groups a1) and a2).

Agents according to the invention may thus exclusively contain keratin hydrolysate(s) in preparation (A), which is or are then present in quantities from 0.1 to 3 wt. %, or may exclusively contain silicone oil(s), which is or are then present in quantities from 0.1 to 5 wt. %, or both keratin hydrolysate(s) and silicone oil(s), which are then present in total quantities of both ingredients from 0.1 to 6 wt. %, in each case based on the weight of preparation (A).

Preferred agents according to the invention are characterized in that preparation (A) includes 0.01 to 1 wt. %, preferably 0.05 to 0.75 wt. %, more preferably 0.1 to 0.5 wt. %, particularly preferably 0.15 to 0.4 wt. %, and in particular 0.2 to 0.3 wt. % hydrolysate(s) having molar masses from 400 to 1200 dalton, obtained from the cortex and/or the cuticle of keratinic fibers.

Further preferred agents according to the invention are characterized in that preparation (A) includes 0.01 to 5 wt. %, preferably 0.05 to 4 wt. %, more preferably 0.1 to 2.5 wt. %, particularly preferably 0.25 to 2 wt. %, and in particular 0.5 to 1.5 wt. % silicone oil(s) from the group of compounds with the INCI name Dimethicone.

Dimethicones may be both linear or branched, and cyclic or cyclic and branched. Linear dimethicones can be described by the following structural formula (Si1):

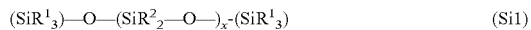

(Si1)

Branched dimethicones can be described by the structural formula (Si1.1):

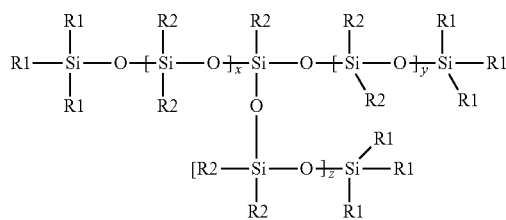

The groups $R^1$ and $R^2$, independently of one another, each denote hydrogen, a methyl group, a C2 to C30 linear saturated or unsaturated hydrocarbon group, a phenyl group and/or an aryl group. Non-limiting examples of the groups represented by $R^1$ and $R^2$ include alkyl groups such as methyl, ethyl, propyl, isopropyl, butyl, isobutyl, pentyl, isopentyl, neopentyl, amyl, isoamyl, hexyl, isohexyl and the like; alkenyl groups such as vinyl, halogen vinyl, alkyl vinyl, allyl, halogen allyl, alkyl allyl; cycloalkyl groups such as cyclobutyl, cyclopentyl, cyclohexyl and the like; phenyl groups, benzyl groups, halogen hydrocarbon groups such as 3-chloropropyl, 4-bromobutyl, 3,3,3-trifluoropropyl, chlorocyclohexyl, bromophenyl, chlorophenyl and the like; and sulfurous groups such as mercaptoethyl, mercaptopropyl, mercaptohexyl, mercaptophenyl and the like; $R^1$ and $R^2$ are preferably alkyl groups containing 1 to approximately 6 carbon atoms, and most preferably $R^1$ and $R^2$ are methyl. Examples of $R^1$ include methylene, propylene, hexamethylene, decamethylene, —CH$_2$CH(CH$_3$)CH$_2$—, phenylen, napthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$ CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—. $R^1$ and $R^2$ are preferably methyl, phenyl and C2 to C22 alkyl groups. Among the C2 to C22 alkyl groups, lauryl, stearyl and behenyl groups are most particularly preferred. The numbers x, y and z are integers and, independently of one another, each range from 0 to 50,000. The molecular weights of the dimethicones range between 1000 D and 10000000 D. The viscosities range between 100 and 10000000 cPs, measured at 25° C. using a glass capillary viscometer according to Dow Corning Corporate Test Method CTM 0004 of Jul. 20, 1970. Preferred viscosities range between 1000 and 5000000 cPs, most particularly preferred viscosities range between 10000 and 3000000 cPs. The range most preferred is between 50000 and 2000000 cPs. Most preferably, viscosities around the range of approximately 60,000 cPs are used. The expression "approximately" defines a deviation from the cited value following the expression "approximately" which is common to the person skilled in the art in technically produced products. Reference shall be made here by way of example to the product "Dow Corning 200 having 60000 cSt."

It goes without saying that the teaching according to the invention also comprises that the dimethicones may already be present in the form of an emulsion.

When the dimethicones are used in the form of an emulsion, according to the invention the droplet size of the emulsified particles is 0.01 µm to 10000 µm, preferably 0.01 to 100 µm, most particularly preferably 0.01 to 20 µm, and most preferably 0.01 to 10 µm. The particle size is determined according to the light scattering method.

Particularly preferred agents according to the invention are characterized in that preparation (A) includes 0.01 to 5 wt. %, preferably 0.05 to 4 wt. %, more preferably 0.1 to 2.5 wt. %, particularly preferably 0.25 to 2 wt. %, and in particular 0.5 to 1.5 wt. % of at least one silicone of formula (Si-I)

(Si-I), were x denotes a number from 0 to 100, preferably from 0 to 50, more preferably from 0 to 20, and in particular 0 to 10.

Further preferred agents according to the invention are characterized in that preparation (A) includes 0.01 to 5 wt. %, preferably 0.05 to 4 wt. %, more preferably 0.1 to 2.5 wt. %, particularly preferably 0.25 to 2 wt. %, and in particular 0.5 to 1.5 wt. % silicone oil(s) from the group of compounds having the INCI name Amodimethicones, wherein compounds having the INCI names Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21 or Silicone Quaternium-22 are preferred.

It has been shown that in particular 4-morpholinomethyl-substituted silicones lead to particularly good care results, without impairing the transparency of the agents. Particularly preferred agents according to the invention are characterized in that preparation (A) includes 0.01 to 5 wt. %, preferably 0.05 to 4 wt. %, more preferably 0.1 to 2.5 wt. %, particularly preferably 0.25 to 2 wt. %, and in particular 0.5 to 1.5 wt. % silicone oil(s) of formula (I)

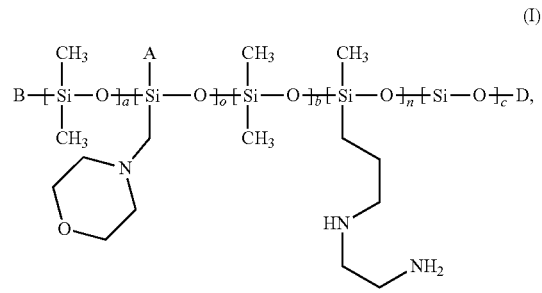

(I)

in which
A denotes a structural unit (I), (II) or (III) bound via an —O—

(I)

(II)

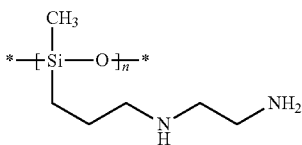

(III)

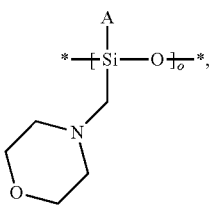

or an oligomeric or polymeric group bound via an —O— and comprising structural units of formulas (I), (II) or (III), or half of a connecting O atom to a structural unit (III), or denotes —OH;
* denotes a bond to one of the structural units (I), (II) or (III) or a terminal group B (Si-bound) or D (O-bound);
B denotes a group —OH, —O—Si(CH$_3$)$_3$, —O—Si(CH$_3$)$_2$OH, —O—Si(CH$_3$)$_2$OCH$_3$;
D denotes a group —H, —Si(CH$_3$)$_3$, —Si(CH$_3$)$_2$OH, —Si(CH$_3$)$_2$OCH$_3$;
a, b and c denote integers between 0 and 1000, with the proviso that a+b+c>0; and
m, n and o denote integers between 1 and 1000.

Such preferred agents contain 0.01 to 5 wt. %, preferably 0.05 to 4 wt. %, more preferably 0.1 to 2.5 wt. %, particularly preferably 0.25 to 2 wt. %, and in particular 0.5 to 1.5 wt. % of at least one 4-morpholinomethyl-substituted silicone of structural formula (I) in preparation (A). This illustrates that the siloxane groups n and o do not necessarily have to be bound directly to a terminal group B or D. Rather, in preferred formulas (I) a>0 or b>0 applies, and in particularly preferred formulas (I) a>0 and b>0 applies, which is to say the terminal group B or D is preferably bound to a dimethylsiloxy group. In formula (I), the siloxane units a, b, c, n and o are also preferably statistically distributed.

The silicones represented by formula (I) and used according to the invention may be trimethylsilyl-terminated on both sides (D=—Si(CH$_3$)$_3$, B=—O—Si(CH$_3$)$_3$); however, they may also be dimethylsilylhydroxy-terminated or dimethylsilylmethoxy-terminated on one side or both sides. Silicones used particularly preferably within the scope of the present invention comprise at least one terminal dimethylsilylhydroxy group, which is to say they are selected from silicones in which the following meanings apply:
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH These silicones result in exorbitant improvements in the properties of hair treated with the agents according to the invention, in particular in a significant reduction of the contact angle.

The structural units of formulas (I), (II) and (III) can be present in the molecule in a statistical distribution; however, the silicones used according to the invention may also be block copolymers composed of blocks of the individual structural units, wherein the blocks may in turn be present again in a statistical distribution. The symbol * at the free valences of the structural units (I), (II) or (III) denotes a bond to one of the structural units (I), (II) or (III) or a terminal group B (Si-bound) or D (O-bound).

In formula (I), group A may denote
a structural unit (I), (II) or (III) bound via an —O—; or
an oligomeric or polymeric group bound via an —O— and containing structural units of formulas (I), (II) or (III); or
half of a connecting O atom to a structural unit (III), or —OH.

In this way, formula (I) is made more precise and becomes one of formulas (Ia), (Ib), (Ic), (Id), (Ie) or (If):

(Ia)

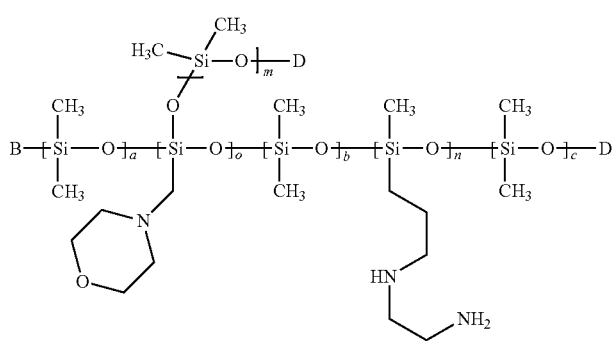

-continued
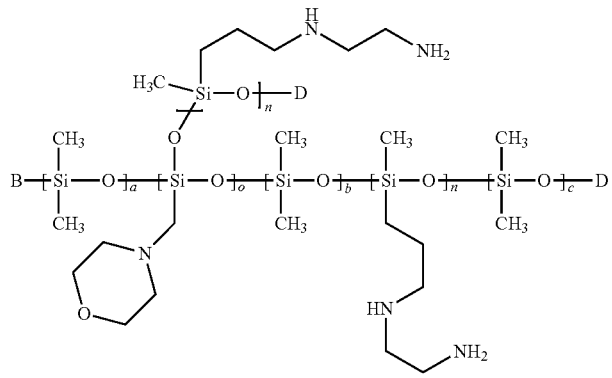
(Ib)
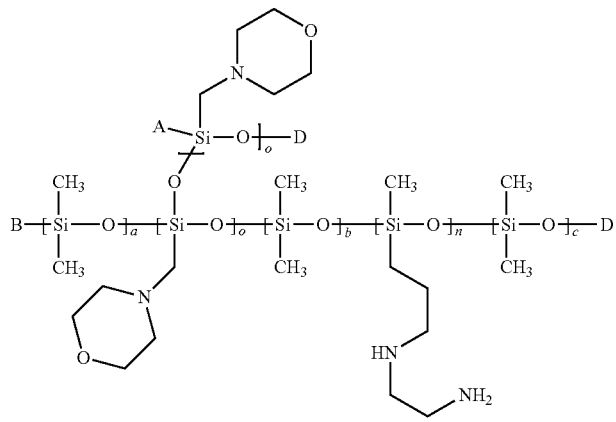
(Ic)
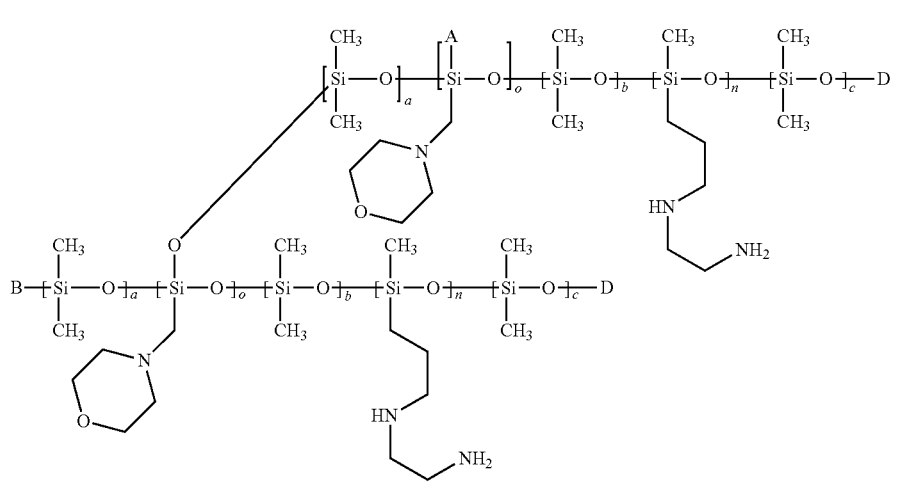
(Id)

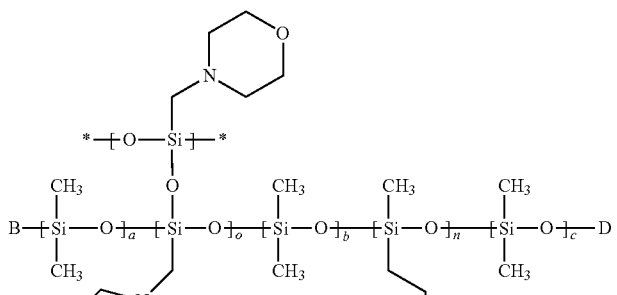

(Ie)

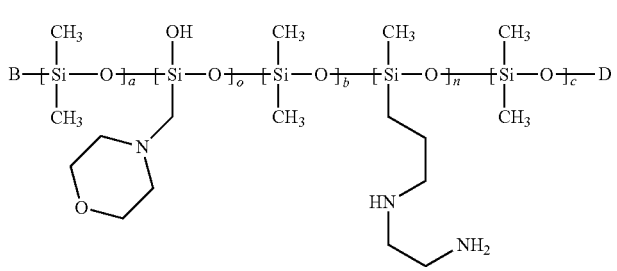

(If)

In structural unit (III), group A may denote
a structural unit (I), (II) or (III) bound via an —O—; or
an oligomeric or polymeric group bound via an —O— and containing structural units of formulas (I), (II) or (III); or
half of a connecting O atom to a structural unit (III), or —OH.

In the first case, the structural unit (III) becomes one of the structural units (IIIa), (IIIb) or (IIIc):

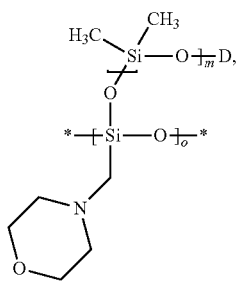

(IIIa)

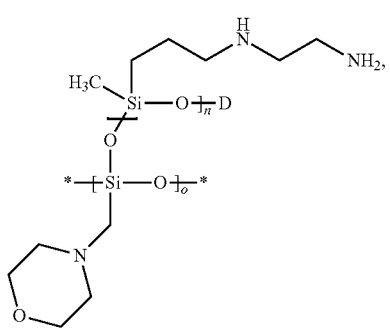

(IIIb)

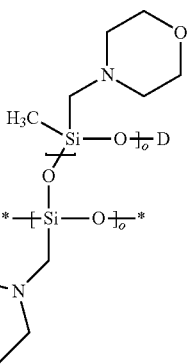

(IIIc)

where m=n=o=1, and A and D are as defined above.

In the second case, the subscripts m, n and o can denote integers between 2 and 1000 in the above-described formulas (IIIa), (IIIb) and (IIIc). However, the second case also covers oligomeric or polymeric groups that contain at least two different structural units of formulas (I), (II) or (III), as represented in formula (IIId):

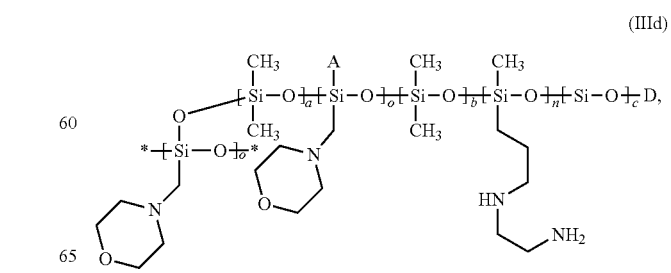

(IIId)

in which a, b and c denote integers between 0 and 1000, with the proviso that a+b+c>0, and n and o denote integers between 1 and 1000.

In the third case, A denotes half of a connecting O atom to a structural unit (III) (shown in structural unit (IIIe) or denotes —OH (shown in structural unit (IIIf).

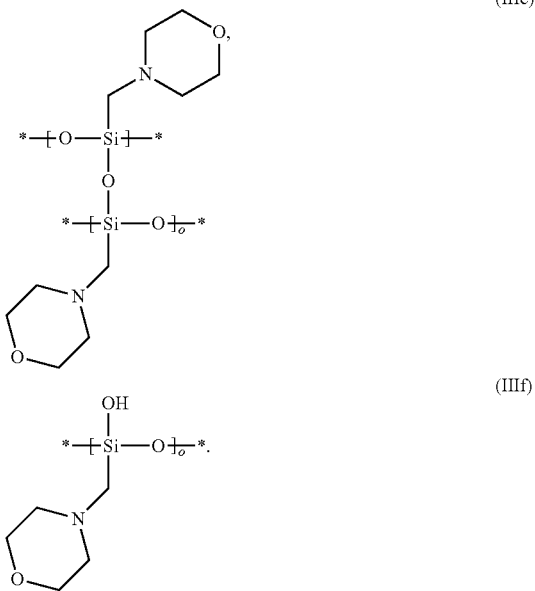

The structural unit (III) or the siloxane units o in formula (I) can form nest or partial cage structures via group A if A denotes half of a connecting O atom to a structural unit (III). Hair treatment agents according to the invention which comprise silicones having corresponding 4-morpholinomethyl-substituted silsesquioxane substructures are preferred according to the invention since these silicones result in enormously improved combability and drastically reduced contact angles.

Preferred agents according to the invention are thus characterized in that composition (A) includes at least one 4-morpholinomethyl-substituted silicone, which comprises structural units of formula (II)

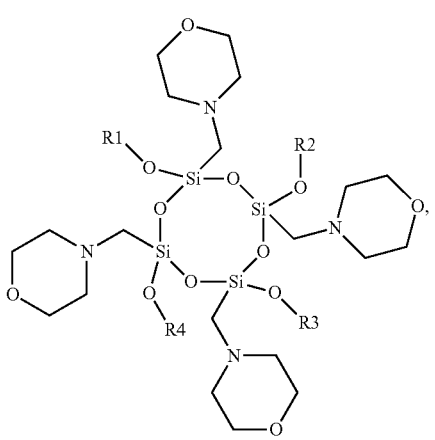

in which
R1, R2, R3 and R4, independently of one another, denote —H, —CH$_3$, a group D, a structural unit (I), (II) or (III), or structural units of formulas (I), (II) or (III) containing an oligomeric or polymeric group; or two of the groups R1, R2, R3 and R4 denote a structural unit —Si(R6)(R5)- where
R5=—CH$_3$, or a structural unit of formula (I) or (II) or (III), or structural units of formulas (I), (II) or (III) containing an oligomeric or polymeric group, or (III);
R6=—OH, —CH$_3$, or a structural unit of formula (I) or (II) or (III), or structural units of formulas (I), (II) or (III) containing an oligomeric or polymeric group, or (III).

In preferred silicones of formula (II), at least one of the groups R1, R2, R3 or R4 denotes an oligomeric or polymeric group containing structural units of formulas (I), (II) or (III). In more preferred silicones of formula (II), at least one of the groups R1, R2, R3 or R4 denotes an oligomeric or polymeric group containing structural units of formulas (I) and (II). In still more preferred silicones of formula (II), at least one of the groups R1, R2, R3 or R4 denotes an oligomeric or polymeric group containing structural units of formulas (I) and (II) and (III).

Preferably at least one of the groups R1, R2, R3 or R4 denotes an —[—Si(CH$_3$)$_2$—O]$_m$ group, which is to say an oligomer or polymer of structural unit (I). Moreover, the structural unit (II) or an oligomer or polymer thereof is preferably never alone, but always bound in the molecule in statistical distribution with further structural units of formula (I) as one of the groups R1, R2, R3 or R4.

Independently of which specific 4-morpholinomethyl-substituted silicone is used in preparation (A), preferred agents according to the invention are those which, in preparation (A), contain a 4-morpholinomethyl-substituted silicone in which more than 50 mole % of the structural units are dimethylsiloxy units, which is to say in which the structural unit (I) accounts for at least half of all structural units of the silicone used.

In other words, silicones in which m>(n+o) or (a+b+c)>(n+o) applies are preferred.

Still more preferred agents are those in which preparation (A) includes a 4-morpholinomethyl-substituted silicone in which more than 90 mole % of the structural units are dimethylsiloxy units, which is to say in which the structural unit (I) accounts for at least nine tenth of all structural units of the silicone used.

In other words, silicones in which m>10(n+o) or (a+b+c)>10(n+o) applies are preferred. Still more preferred cosmetic agents contain a 4-morpholinomethyl-substituted silicone in which more than 98 mole % of the structural units are dimethylsiloxy units, which is to say in which the structural unit (I) accounts for ninety-eight one hundredth of all structural units of the silicone used.

In other words, silicones in which m>50(n+o) or (a+b+c)>50(n+o) applies are preferred. Still more preferred cosmetic agents contain a 4-morpholinomethyl-substituted silicone in which more than 98.5 mole % of the structural units are dimethylsiloxy units, which is to say in which the structural unit (I) accounts for nine hundred eighty-five thousandth of all structural units of the silicone used.

In other words, silicones in which m>75(n+o) or (a+b+c)>75(n+o) applies are preferred. Still more preferred cosmetic agents contain a 4-morpholinomethyl-substituted silicone in which more than 99 mole % of the structural units are dimethylsiloxy units, which is to say in which the structural unit (I) accounts for nine tenth of all structural units of the silicone used.

In other words, silicones in which m>100(n+o) or (a+b+c)>100(n+o) applies are preferred.

In summary, preferred agents according to the invention are characterized by containing, in preparation (A), at least one 4-morpholinomethyl-substituted silicone in which
m>(n+o) or (a+b+c)>(n+o), preferably
m>10(n+o) or (a+b+c)>10(n+o), particularly preferably
m>50(n+o) or (a+b+c)>50(n+o), more preferably
m>75(n+o) or (a+b+c)>75(n+o), and in particular
m>100(n+o) or (a+b+c)>100(n+o) applies.

It has been shown that the effect of the silicones used according to the invention can be further increased when certain nonionic components are likewise used in the agents according to the invention. Moreover, these nonionic components have positive effects on the storage stability of the agents according to the invention. Nonionic components that are particularly suited here are ethoxylates of decanol, undecanol, dodecanol, tridecanol and so forth. Ethoxylated tridecanols have proven to be particularly suited, which are particularly preferably incorporated into the agents according to the invention. Particularly preferred cosmetic compositions according to the invention contain 0.00001 to 5 wt. %, preferably 0.0001 to 3.5 wt. %, particularly preferably 0.001 to 2 wt. %, more preferably 0.01 to 1 wt. %, and in particular 0.1 to 0.5 wt. % branched, ethoxylated tridecanol (INCI name: Trideceth-5) or α-iso-tridecyl-ω-hydroxy polyglycol ether (INCI name: Trideceth-10), or the mixtures thereof, based on the weight of the cosmetic compositions.

Preferred morpholinomethyl-substituted silicone(s) according to the invention comprise both hydroxyals and alkoxy groups. Particularly preferred agents according to the invention contain, in preparation (A), hydroxy-terminated 4-morpholinomethyl-substituted silicone(s) in which the hydroxy/alkoxy molar ratio ranges from 0.2:1 to 0.4:1, preferably from 1:0.8 to 1:1.1.

The average molecular weight of the silicone is preferably from 2,000 to 200,000, and still more preferably from 5,000 to 100,000, in particular 10,000 to 50,000 daltons. Cosmetic compositions in which the weight-average molar mass of the 4-morpholinomethyl-substituted silicone of formula (I) present in these compositions ranges from 2,000 to 1,000,000 gmol$^{-1}$, preferably from 5,000 to 200,000 gmol$^{-1}$, are preferred.

The average molecular weights of amino-substituted silicones can be measured by way of gel permeation chromatography (GPC) at room temperature in polystyrene, for example. μ-Styragel columns may be selected as columns, THF may be selected as the eluent, and 1 ml/min may be the selected flow rate. The detection is preferably carried out by way of refractometry and a UV meter.

The first subject matter of the invention comprises agents for lightening keratinic fibers, which contain at least two preparations (A) and (B) packaged separately from each other, and optionally a further preparation (C) packaged separately from (A) and (B). Preparations (B), and optionally (C), contain the active ingredients in a flowable cosmetic carrier. The base substance of the flowable cosmetic carrier is preferably aqueous or aqueous-alcoholic. For hair bleaching purposes, such carriers are transparent gels, or surfactant-containing foaming solutions, for example, such as shampoos, foam aerosols or other preparations suitable for use on hair. Within the meaning of the invention, a preferred flowable carrier includes at least 40 wt. %, in particular at least 50 wt. % water. Aqueous-alcoholic carriers within the meaning of the present invention shall be understood to mean compositions containing water and 3 to 70 wt. % of a $C_1$-$C_4$ alcohol, in particular ethanol or isopropanol. The agents according to the invention may additionally contain further organic solvents, such as methoxybutanol, ethyldiglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred.

Preparations (B) and/or preparations (C) of the blonding agent according to the invention contain at least one natural polymer as an essential ingredient.

If the agent for lightening keratinic fibers includes exactly two preparations (A) and (B) packaged separately from each other, which are mixed immediately before use to form an application mixture, then preparation (B) according to the invention includes at least one natural polymer.

If the agent for lightening keratinic fibers includes at least three preparations (A), (B) and (C) packaged separately from each other, which are mixed immediately before use to form an application mixture, then preparation (B) and/or preparation (C) may contain at least one natural polymer.

Cellulose derivatives that are utilized as thickening agents can be used, for example, as the natural polymer. Examples are agar-agar, carrageenan, alginates, xanthan gum, karaya gum, ghatti gum, tragacanth, scleroglucan gums or gum arabic, alginates, pectins, polyoses, guar gums, locust bean gum, linseed gums, dextrans, pectins, starch fractions and derivatives such as amylose, amylopectin, and dextrins, gelatins, and casein, as well as cellulose derivatives such as methyl cellulose, carboxyalkyl celluloses such as carboxymethyl cellulose, and hydroxyalkyl celluloses such as hydroxyethyl cellulose.

Natural polymers from the described substance classes are commercially available and are offered, for example, under the trade names Deuteron®-XG (anionic heteropolysaccharide based on β-D-glucose, D-manose, D-glucuronic acid, Schoener GmbH), Deuteron®-XN (nonionogenic polysaccharide, Schoener GmbH), Protanal RF 6650 alginate (sodium alginate, FMC Biopolymer), Cekol (cellulose gum, Kelco), Kelzan (xanthan biopolymer, Kelco), Xanthan FN (xanthan biopolymer, Jungbunzlauer), Keltrol, for example Keltrol CG-T (xanthan biopolymer, Kelco) or Keltrol CG-SFT (xanthan biopolymer, Kelco).

In a preferred embodiment of the invention, preparations (B) and/or optionally (C) contain xanthan.

Preferred xanthans according to the invention are those that yield transparent preparations after swelling. Use of the xanthan biopolymer is particularly preferred, which is marketed under the trade name Keltrol CG-SFT by Kelco.

In a preferred embodiment, preparation (B), based on the weight thereof, includes xanthan in quantities from 0.1 to 10 wt. %, preferably from 0.5 to 6 wt. %, particularly preferably from 0.7 to 5 wt. %, and more particularly preferably from 1 to 4 wt. %, explicitly 1, 2, 3, or 4 wt. %, if the agent for lightening keratinic fibers includes exactly two preparations (A) and (B) packaged separately from one another, which are mixed immediately before use to from an application mixture. The ready-to-use application preparations preferably contain xanthan in quantities from 0.6 to 5 wt. %, particularly preferably from 1.0 to 3.5 wt. %, and more particularly preferably from 1.5 to 2.5 wt. %, explicitly 1.5, 1.6, 1.7, 1.8, 1.9, 2.0, 2.1, 2.2, 2.3, 2.4, or 2.5 wt. %, based on the weight of the preparations.

If the agent for lightening keratinic fibers includes at least three preparations (A), (B) and (C) packaged separately from each other, which are mixed immediately before use to form an application mixture, then preparation (B) and/or preparation (C) may contain xanthan. If the agent for lightening keratinic fibers includes at least three preparations (A), (B) and (C) packaged separately from each other, which are mixed immediately before use to form an application mixture, preparations in which preparation (C) includes xanthan are preferred. Preparations in which preparation (C) includes xanthan and preparation (B) is free from xanthan are more particularly preferred.

Independently of whether preparation (B) and/or preparation (C) contain xanthan, preferred completely mixed application preparations are those which contain xanthan in quantities from 0.6 to 5 wt. %, particularly preferably from 1.0 to 3.5 wt. %, and more particularly preferably 1.5 to 2.5 wt. %, explicitly 1.5, 1.6, 1.7, 1.8, 1.9, 2.0, 2.1, 2.2, 2.3, 2.4, or 2.5 wt. %, based on the weight of the completely mixed application preparation.

In one particular embodiment, preparations (B) according to the invention contain hydrogen peroxide as the oxidizing agent.

The concentration of a hydrogen peroxide solution in the oxidizing agent preparation (B) is determined by legal requirements on the one hand, and by the desired effect on the other hand. Preparations (B) preferably contain hydrogen peroxide in quantities from 0.5 to 30 wt. %, preferably from 1 to 20 wt. %, particularly preferably from 5 to 15 wt. %, and more particularly preferably from 6 to 12 wt. %, explicitly 6, 7, 8, 9, 10, 11, or 12 wt. %, based on the weight of the preparations.

Preferred ready-to-use agents according to the invention are characterized by comprising 0.01 to 12 wt. %, preferably 0.1 to 10 wt. %, particularly preferably 1 to 8 wt. % hydrogen peroxide, based on the total weight of the ready-to-use agent.

Particularly preferred agents according to the invention are characterized in that preparation (B)—based on the weight thereof—includes 0.1 to 10 wt. %, preferably 0.25 to 7.5 wt. %, more preferably 0.5 to 5 wt. %, particularly preferably 0.75 to 4 wt. %, and in particular 1 to 2.5 wt. % xanthan, and 0.5 to 30 wt. %, preferably 1 to 20 wt. %, particularly preferably 5 to 15 wt. %, and in particular 6 to 12 wt. % hydrogen peroxide, calculated as 100% $H_2O_2$.

To stabilize the hydrogen peroxide, the pH value of preparation (B) may preferably be set to a pH of 3 to 5, particularly preferably to a pH of 3.5 to 4.5, and more particularly preferably to a pH of 3.8 to 4.2.

The viscous properties of preparation (B) are important for good miscibility and high stability of the preparation. In a preferred embodiment, preparations (B) of the present invention are characterized by having a viscosity from 1,000 mPa·s to 50,000 mPa·s, preferably from 5,000 mPa·s to 45,000 mPa·s, and particularly preferably from 7,000 mPa·s to 40,000 mPa·s during measurements in a rotational viscometer from Brookfield, spindle size 4, at 25° C. and 4 rpm. The completely mixed and ready-to-use agents preferably have a viscosity from 10,000 mPa·s to 50,000 mPa·s, and particularly preferably from 18,000 mPa·s to 30,000 mPa·s during measurements with a rotational viscometer from Brookfield, spindle size 5, at 25° C. and 4 rpm.

Moreover, setting the pH value is important for good miscibility and stability. Completely mixed and ready-to-use agents having a pH value between 9 and 12 are preferred according to the invention.

It may moreover be advantageous according to the invention if preparation (B) includes at least one nonionic surfactant, preferably at least one ethoxylated fatty alcohol having 40 to 60 ethylene oxide units. According to the invention, this shall be understood to mean an addition product of ethylene oxide to a fatty alcohol. Fatty alcohols are saturated and unsaturated alcohols having 12 to 24 C atoms, which can be linear or branched. The mole amount of ethylene oxide used per mole of fatty alcohol denotes the degree of ethoxylation understood. Suitable nonionic surfactants are in particular ethylene oxide addition products to octyl alcohol (caprylic alcohol), nonyl alcohol (pelargonic alcohol), undecyl alcohol, undec-10-ene-1-ol, dodecyl alcohol (lauryl alcohol), 2,6,8-trimethyl-4-nonanol (isolauryl alcohol), tridecyl alcohol, tetradecyl alcohol (myristyl alcohol), pentadecyl alcohol, hexadecyl alcohol (cetyl/palmityl alcohol), heptadecyl alcohol, octadecyl alcohol (stearyl alcohol), isostearyl alcohol, (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), nonadecan-1-ol (nonadecyl alcohol), eicosan-1-ol (eicosyl alcohol/arachyl alcohol), (9Z)-eicos-9-en-1-ol (gadoleyl alcohol), (5Z,8Z,11Z,14Z)-eicosa-5,8,11,14-tetraen-1-ol (arachidyl alcohol), heneicosyl alcohol, docosyl alcohol (behenyl alcohol), (13Z)-docos-13-en-1-ol (erucyl alcohol) or (13E)-docosen-1-ol (brassidyl alcohol). It is likewise possible according to the invention to use mixtures of fatty alcohols which are obtained by deliberate mixing, or else by production processes. Examples include coconut alcohol (mixture of $C_8$-$C_{18}$ fatty alcohols) or cetearyl alcohol (1:1 mixture of $C_{16}$ and $C_{18}$ fatty alcohols).

Degrees of ethoxylation from 20 to 60 are preferred. Preferred nonionic surfactants according to the invention of the ethoxylated fatty alcohol type are Ceteareth-20 and Ceteareth-50.

The blonding agents may moreover contain alkalizing agents. Preferred alkalizing agents are, for example, ammonia, alkanolamines, basic amino acids, and inorganic alkalizing agents such as alkali metal or alkaline earth metal hydroxides, alkali metal or alkaline earth metal metasilicates, alkali metal or alkaline earth metal phosphates, and alkali metal or alkaline earth metal hydrogen phosphates. Preferred metal ions are lithium, sodium and/or potassium. Ammonia is a particularly preferred alkalizing agent.

Inorganic alkalizing agents that can be used according to the invention are preferably selected from sodium hydroxide, potassium hydroxide, calcium hydroxide, barium hydroxide, sodium phosphate, potassium phosphate, sodium silicate, potassium silicate, magnesium silicate, sodium carbonate and potassium carbonate. Sodium hydroxide and/or potassium hydroxide are particularly preferred.

Alkalizing agents that can be used according to the invention are preferably selected from alkanolamines composed of primary, secondary or tertiary amines having a C2-C6 alkyl basic structure, which carries at least one hydroxyl group. Particularly preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol(monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-1,3-diol, 2-amino-2-ethyl-1,3-propanediol, N,N-dimethyl-ethanolamine, methylglucamine, triethanolamine, diethanolamine and triisopropanolamine. Particularly preferred alkanolamines are monoethanolamine, 2-amino-2-methylpropanol and triethanolamine.

The basic amino acids that can be used as the alkalizing agent according to the invention are preferably selected from the group consisting of L-arginine, D-arginine, D/L-arginine, L-lysine, D-lysine, D/L-lysine, L-ornithine, D-ornithine, D/L-ornithine, L-histidine, D-histidine and/or D/L-histidine. L-arginine, D-arginine and/or D/L-arginine are particularly preferred as an alkalizing agent within the meaning of the invention.

Some customer find the intense odor development of ammonia to be bothersome or annoying. While ammonia is a preferred alkalizing agent, ready-to-use preparations that are free from ammonia may thus be preferred according to the invention. Preferred alkalizing agents for preparations that are free from ammonia are monoethanolamine, 2-amino-2-methyl-propanol and triethanolamine.

If the ready-to-use mixtures contain alkalizing agents, preferred preparations according to the invention are those containing alkalizing agents in a quantity from 0.05 to 20 wt. %, in particular from 0.5 to 10 wt. %, in each case based on the total weight of the ready-to-use agent.

In a further embodiment of the invention, preparations (A) and (B) may be mixed with further separately packaged preparations immediately before use to form an application mixture.

In a preferred embodiment of the invention, the agent according to the invention additionally includes at least one further preparation (C) packaged separately from preparations (A) and (B), wherein preparation (C) includes at least one alkalizing agent and at least one natural polymer.

Preparation (C) preferably includes natural polymers, which were already mentioned above in the text in connection with preparation (B).

Preferred alkalizing agents according to the invention are those that were already described above.

If preparations (C) contain alkalizing agents, preferred preparations according to the invention are those containing alkalizing agents in a quantity from 0.05 to 20 wt. %, in particular from 0.5 to 10 wt. %, in each case based on the total weight of the ready-to-use agent.

Independently of whether preparations (C) and/or preparation (B) and/or further preparations contain alkalizing agents, preferred preparations according to the invention when using alkalizing agents are those containing alkalizing agents in a quantity from 0.05 to 20 wt. %, in particular from 0.5 to 10 wt. %, in each case based on the total weight of the ready-to-use agent.

So as to further increase the lightening performance, a silicon-containing compound may additionally be added to preparation (C) as a bleach accelerator. This compound is preferably selected from the group consisting of silicic acid, alkali metal silicates, and alkaline earth metal silicates.

While small amounts of the silicon-containing compounds already increase the lightening performance, it may be preferred according to the invention to use the silicon-containing compounds in quantities from 0.05 wt. % to 50 wt. %, preferably in quantities from 0.5 wt. % to 30 wt. %, and particularly preferably in quantities from 1.0 wt. % to 25 wt. %, in each case based on the total weight of preparation (C).

In particular, alkali metal silicates in the form of waterglass are used as silicon-containing compounds. Waterglass shall be understood to mean a compound formed from a silicate of formula $(SiO_2)_n(Na_2O)_m(K_2O)_p$, where n denotes a positive rational number and m and p, independently of one another, denote a positive rational number or 0, with the proviso that at least one of the parameters m or p is different from 0 and the ratio of n to the sum of m and p is between 2:1 and 4:1.

In addition to the components described by the empirical formula, the waterglasses may contain further additives, such as phosphates or magnesium salts, in small quantities. Particularly preferred waterglasses according to the invention are marketed, among other things, by the designations Ferrosil® 119, Soda Waterglass 40/42, Portil® A, Portil® AW and Portil® W, and Britesil® C20.

Moreover, in particular silicic acids may be used as silicon-containing compounds, which are also marketed as silica or silica gel. A silica gel marketed by the trade name Aerosil 200 (INCI name: Silica) is preferred.

The lightening or blonding agents may moreover contain additional bleaching power enhancers so as to enhance the blonding action. Compounds that, under perhydrolysis conditions, yield aliphatic peroxocarboxylic acids having preferably 1 to 10 C-atoms, in particular 2 to 4 C-atoms, and/or optionally substituted perbenzoic acid, can be used as bleaching power enhancers. Polyacylated alkylenediamines, in particular tetra acetyl ethylene diamine (TAED), acylated triazine derivatives, in particular 1,5-diacetyl-2,4-dioxo-hexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or iso-nonanoyl oxybenzene sulfonate (n- or i-NOBS), carboxylic acid anhydrides, in particular phthalic anhydride, acylated polyhydric alcohols, in particular triacetin, ethylene glycol diacetate and 2,5-diacetoxy-2,5-dihydrofurane are preferred.

Carbonate salts or hydrogen carbonate salts may preferably be used according to the invention as bleach boosters of the carbonic acid derivative type. These are preferably selected from the group of ammonium salts, alkali metal (in particular Na and K), and alkaline earth metal (in particular Mg and Ca) salts, carbonate salts or hydrogen carbonate salts. Particularly preferred carbonate salts or hydrogen carbonate salts are ammonium hydrogen carbonate, ammonium carbonate, sodium hydrogen carbonate, sodium carbonate, potassium hydrogen carbonate, potassium carbonate, magnesium carbonate, and calcium carbonate. These particularly preferred salts may be used alone or in mixtures of at least two representatives as bleach boosters. Alkyl carbonates and carbamates and silyl carbonates and carbamates are also suitable bleach boosters.

Moreover, bleaching power enhancers that may be used according to the invention may be selected from nitrogenous, optionally cationic heterocycles, in particular imidazole.

Particularly preferred nitrogenous heterocyclic bleaching power enhancers are the quaternized cations of pyridines and 3,4-dihydroisoquino lines, such as salts of 4-acetyl-1-methylpyridinium, in particular 4-acetyl-1-methylpyridinium-p-toluene sulfonate, salts of 2-acetyl-1-methylpyridinium, in particular 2-acetyl-1-methylpyridinium-p-toluene sulfonate, and salts of N-methyl-3,4-dihydroisoquinolinium, in particular N-methyl-3,4-dihydroisoquinolinium-p-toluene sulfonate.

Urea is another bleaching power enhancer that may be used according to the invention.

Bleaching power enhancers may be present in preparation (A) and/or preparation (B) and/or optionally in preparation (C) and/or optionally in further preparations. The bleaching power enhancers may either be present in only one of the preparations, or in two or more of the preparations. Hydrolysis-sensitive bleaching power enhancers can preferably be used in the powdery preparation (A). Independently of whether bleaching power enhancers are used in preparation (A) and/or preparation (B) and/or preparation (C) and/or further preparations, when bleaching power enhancers are used these are preferably present in quantities from 0.5 to 30 wt. %, in particular in quantities from 2 to 20 wt. %, in each case based on the total weight of the completely mixed blonding preparation.

Moreover, the lightening or blonding agents may contain certain direct dyes of complementary colors for the purpose of matting undesirable residual color impressions, in particular in the red or blue range. These are dyes that attach directly to the hair and require no oxidative process to develop the color. Direct dyes are usually nitrophenylene diamines, nitroaminophenols, azo dyes, anthraquinones or indophenols. Direct dyes are known as anionic, cationic and nonionic direct dyes. The direct dyes are preferably used each in a quantity from 0.001 to 2 wt. %, based on the total application preparation.

Preferred anionic direct dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 1, Acid Green 50, Acid Violet 43, Acid Black 1, Acid Black 52, bromophenol blue and tetrabromophenol blue. Preferred cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B), and direct dyes that contain a heterocycle having at least one quaternary nitrogen atom, in particular Basic Yellow 87, Basic Orange 31 and Basic Red 51. The cationic direct dyes that are sold under the trademark Arianor are cationic direct dyes that are likewise preferred according to the invention. In particular nonionic nitro and quinone dyes and neutral azo dyes are suited as nonionic direct dyes. Preferred nonionic direct dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 11, Disperse Violet 1, Disperse Violet 4, Disperse Black 9, as well as 1.4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-ntro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol. Agents that contain at least one combination of tetrabromophenol blue and Acid Red 92 are most particularly preferred.

It has furthermore proven advantageous for the ready-to-use agents to contain at least one stabilizer or complexing agent. Particularly preferred stabilizers are phenacetin, alkali benzoates (sodium benzoate) and salicylic acids. Furthermore all complexing agents from the prior art may be used. These may belong to different chemical groups. Preferably are used individually or together in the mixture. Preferred complexing agents according to the invention are nitrogenous polycarboxylic acids, in particular EDTA, and phosphonates, preferably hydroxyalkane or aminoalkane phosphonates, and in particular 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof.

The agents according to the invention can moreover contain further active ingredients, auxiliary substances and additives, for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or non-volatile, straight, branched or cyclic, cross-linked or non-cross-linked polyalkylsiloxanes (such as dimethicone or cyclomethicone), polyarylsiloxanes and/or polyalkylarylsiloxanes, in particular polysiloxanes having organofunctional groups, such as substituted or unsubstituted amines (amodimethicone), carboxyl groups, alkoxy groups and/or hydroxyl groups (dimethicone copolyols), linear polysiloxane (A)-polyoxyalkylene (B) block copolymers, grafted silicone polymers; cationic polymers such as quaternized cellulose ethers, polysiloxanes having quaternary groups, dimethyl diallyl ammonium chloride polymers, acrylamide/dimethyl diallyl ammonium chloride copolymers, dimethylaminoethyl methacrylate/vinylpyrrolidinone copolymers quaternized with diethyl sulfate, vinylpyrrolidinone/imidazolinium methochloride copolymers and quaternized polyvinyl alcohol; zwitterionic and amphoteric polymers; anionic polymers such as polyacrylic acids or cross-linked polyacrylic acids; structurants such as glucose, maleic acid and lactic acid, hair-conditioning compounds such as phospholipids, for example lecithin and cephalins; perfume oils, dimethylisosorbide and cyclodextrins; fiber structure-improving active agents, in particular monosaccharides, disaccharides and oligosaccharides such as glucose, galactose, fructose, fructose and lactose; dyes for coloring the agent; antidandruff active agents such as piroctone olamine, Zinc Omadine and climbazole; amino acids and oligopeptides, in particular arginine and/or serine; animal- and/or plant-based protein hydrolysates such as elastin, collagen, keratin, silk and milk protein hydrolysates, or almond, rice, pea, potato and wheat protein hydrolysates, and in the form of the fatty acid condensation products thereof, or optionally the anionic or cationic modified derivatives thereof; sunscreen agents such as derivatized benzophenones, cinnamic acid derivatives and triazines; active ingredients such as panthenol, pantothenic acid, pantolactone, allantoin, pyrrolidinone carboxylic acids and salts thereof and bisabolol; polyphenols, in particular hydroxycinnamic acids, 6,7-dihydroxycoumarin, hydroxybenzoic acids, catechines, tannins, leucoanthocyanidins, anthocyanidins, flavanones, flavones and flavonols; ceramides or pseudoceramides; vitamins, provitamins and vitamin precursors, in particular of the groups A, $B_3$, $B_5$, $B_6$, C, E, F and H; plant extracts; swelling and penetration substances such as glycerol, propylene glycol monoethyl ether, carbonates, hydrogen carbonates, guanidines, ureas and primary, secondary and tertiary phosphates; pearlizing agents such as ethylene glycol monostearate and distearate and PEG-3 distearate; pigments, and blowing agents such as propane-butane mixtures, $N_2O$, dimethyl ether, $CO_2$ and air.

Particularly preferred according to the invention are active ingredients, auxiliary substances and additives that, in combination with the agent according to the invention, yield a transparent application mixture.

A person skilled in the art will select these further substances as a function of the desired properties of the agents. With respect to further optional components and the quantities of these components used, reference is expressly made to the relevant manuals known to the person skilled in the art, such as Kh. Schrader, Grundlagen and Rezepturen der Kosmetika (Fundamentals and Formulations of Cosmetics), 2nd edition, Hüthig Buch Verlag, Heidelberg, 1989. The respective additional active ingredients and auxiliary substances are preferably used in the agents according to the invention in quantities from 0.0001 to 10 wt. %, in particular from 0.0005 to 5 wt. %, based on the total weight of the application mixture.

A second subject matter of the invention is a method for changing the color of keratinic fibers, in which at least two preparations (A) and (B) packaged separately from each other, of which preparation (A) includes at least one persulfate and preparation (B) includes at least one oxidizing agent, are mixed to form an application mixture, this mixture is applied to the fibers and rinsed off again after an exposure time, characterized in that
  i. preparation (B) and/or an optionally present preparation (C) comprise at least one natural polymer,
  ii. preparation (A)—based on the weight thereof—comprises
    a1) 0 to 3 wt. % keratin hydrolysate(s) and/or
    a2) 0 to 5 wt. % silicone oil(s),
with the proviso that preparation (A)—based on the weight thereof—comprises 0.1 to 6 wt. % compound(s) from groups a1) and a2).

The ready-to-use agents are prepared immediately before use on the hair by mixing the two preparations (A) and (B) and optionally a third preparation (C) and/or further preparations. In ready-to-use agents that are mixed from more than two preparations to form a completely mixed application mixture, it may be immaterial whether initially two preparations are mixed together and subsequently the third preparation is added and mixed in, or whether all preparations are combined at once and subsequently mixed. Mixing can be carried out by stirring in a bowl or a cup or by shaking in a closable container.

The term "immediately" shall be understood to mean a time period from a few seconds to one hour, preferably up to 30 min, in particular up to 15 min.

The agents according to the invention are used in a method for lightening keratinic fibers, in particular human hair, in which the agent is applied to the keratin-containing fibers, allowed to remain on the fibers at a temperature from room temperature to 45° C. for an exposure duration of 10 to 60 minutes, and subsequently rinsed off again using water or washed off using a shampoo.

The exposure time of the ready-to-use lightening agents is preferably 10 to 60 min, in particular 15 to 50 min, particularly preferably 20 to 45 min. During the exposure time of the agent on the fiber, it may be advantageous to support the lightening process by supplying heat. The heat can be supplied by an external heat source, such as by way of a hot air blower, or by the body temperature of the subject, in particular when the hair of a living subject is lightened. If the latter option applies, the section to be lightened is usually covered with a cap. An exposure phase at room temperature is likewise covered by the invention. The temperature is preferably between 20° C. and 40° C., in particular between 25° C. and 38° C., during the exposure time. The lightening agents already yield good blonding and lightening results at physiologically compatible temperatures of less than 45° C.

After the exposure time has ended, the remaining lightening preparation is rinsed off the hair using water or a cleaning agent. In particular commercially available shampoo may be used as the cleaning agent, wherein the cleaning agent can be dispensed with and the rinsing process can be carried out using tap water in particular when the lightening agent includes a strong surfactant-containing carrier.

A preferred method is characterized in that the degree of lightening of the keratinic fiber during the exposure time is checked visually without removing the application mixture from the fiber. For this purpose, a ready-to-use transparent agent of the first subject matter of the invention is applied to human hair, and the lightening process is assessed once or multiple times during the exposure time by visual checking, without removing the agent from the fiber. In this way, simplified and constant monitoring of the decolorizing process is ensured.

"Transparent" within the meaning of the invention refers to preparations which are clear when a uniform layer of these preparations is applied in a thickness from 1 to 3 mm to a substrate and through which the human eye is able to detect and assess the color of the substrate without haze. Transparency can moreover be measured by a person skilled in the art using technical methods. "Transparent" within the meaning of the invention therefore also refers to preparations that achieve transmissions of at least 70%, in particular at least 80%, in photometric measurements using a Methrom 662 Photometer at 25° C.

Preferred methods according to the invention are characterized in that the degree of lightening of the keratinic fiber during the exposure time is checked visually without removing the application mixture from the fiber.

The preferred embodiments of the first subject matter of the invention apply, mutatis mutandis, also to the second subject matter of the invention.

A third subject matter of the invention is the use of keratin hydrolysates and/or silicone oils to increase the lightening and care performance of transparent blonding agents. The embodiments of the preceding subject matter of the invention apply, mutatis mutandis, with respect to preferred embodiments of the uses according to the invention.

EXAMPLES

Example 1

Composition of Preparation (A) for Blonding Agents Composed of Two Preparations

| Description | A1 | A2 | A3 | A4 | A5 | A6 | A7 | A8 |
| --- | --- | --- | --- | --- | --- | --- | --- | --- |
| EDTA Na2 | 1.51 | 1 | 1.51 | 1.51 | 1.51 | 1.51 | 1.51 | 1.51 |
| Magnesium | 8.0 | 7.5 | 7.0 | 8.5 | 9.0 | 8.0 | 8.0 | 8.0 |
| Aerosil 200 | 3.02 | 1 | 3 | 3 | 3 | 3 | 3 | 3 |
| Sodium metasilicate | 4.7 | 5.0 | 5.5 | 4.0 | 4.5 | 4.7 | 4.7 | 4.7 |
| Sodium disilicate | 31.05 | 30.0 | 31.0 | 30.5 | 31.5 | 31.05 | 31.0 | 31.0 |
| Rohagit S hv | 2.75 | 4.05 | 1 | | | 2.5 | 3.5 | |
| CEKOL 50000 | 1.1 | 1.0 | 1.5 | 1.0 | 1.1 | 1.1 | | |
| Ammonium persulfate + 0.5% | 10.0 | 10.0 | 10.0 | 10.0 | 10.0 | 10.0 | 10.0 | 10.0 |
| Potassium persulfate | 30.0 | 30.0 | 30.0 | 30.0 | 30.0 | 30.0 | 30.0 | 30.0 |
| Sodium persulfate | 4.0 | 4.0 | 4.0 | 4.0 | 4.0 | 4.0 | 4.0 | 4.0 |

-continued

| Description | A1 | A2 | A3 | A4 | A5 | A6 | A7 | A8 |
|---|---|---|---|---|---|---|---|---|
| Paraffinum | 3.6 | 3.6 | 3.6 | 3.6 | 3.6 | 3.6 | 3.6 | 3.6 |
| Perfume | 0.2 | 0.2 | 0.2 | 0.2 | 0.2 | 0.2 | 0.2 | 0.2 |
| Dimethicone, 60,000 | 0.2 | 0.1 | | | 0.1 | 0.15 | 0.2 | 0.2 |
| Keratin hydrolysate, | 1.5 | 1.5 | 2.0 | 1.5 | | | | 1.5 |

*raw materials used: Aerosil 200 (INCI name: Silica (Evonik Degussa)), Rohagit S hv (INCI name: Acrylates Copolymer (Evonik Röhm)), CEKOL 50000 (INCI name: Cellulose Gum (CP Kelco)), LAPONITE XLG (INCI name: Sodium Magnesium Silicate (Roockwood Additives)), LAPONITE XLS (INCI name: Sodium Magnesium Silicate and Tetrasodium Pyrophosphate (Roockwood Additives)).

Example 2

Composition of Preparation (B) for Blonding Agents Composed of Two Preparations

| Description | B1 | B2 | B3 | B4 | B5 |
|---|---|---|---|---|---|
| Water, deionized | up to 100 | up to 100 | up to 100 | up to 100 | up to 100 |
| Sodium hydroxide 45% | 0.73 | 0.73 | 0.73 | 0.73 | 0.73 |
| Dipicolinic acid | 0.1 | 0.1 | 0.1 | 0.1 | 0.1 |
| Disodium pyrophosphate | 0.03 | 0.03 | 0.03 | 0.03 | 0.03 |
| HEDP 60% | 1.5 | 1.5 | 1.5 | 1.5 | 1.5 |
| Keltrol CG-SFT | 2 | | 1.5 | 1 | 0.5 |
| 1,2-propanediol | 4 | 2 | 4 | 4 | 4 |
| Hydrogen peroxide 50% | 18 | 18 | 18 | 18 | 18 |

*raw materials used: Keltrol CG-SFT (INCI name: Xanthan Gum (CP Kelco)).
Preparations B1 to B5 are transparent gels.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, comprising at least two preparations (A) and (B) packaged separately from each other, and optionally a further preparation (C) packaged separately from (A) and (B), which are mixed immediately before use to form an application mixture, wherein
    preparation (A) comprises 5 to 60 wt % of, based on the weight thereof, of at least one persulfate selected from selected from the group consisting of ammonium peroxodisulfate, potassium peroxodisulfate, and sodium peroxodisulfate, and is free from xanthan;
    preparation (B) is flowable and includes at least one oxidizing agent and, based on the weight thereof, 0.1 to 10 wt % xanthan and 0.5 to 30 wt % hydrogen peroxide, calculated as 100% $H_2O_2$ and
    preparation (B) or preparation (C) contain at least one polymer selected from the group consisting of agar-agar, carrageenan, alginates, xanthan gum, karaya gum, ghatti gum, tragacanth, scleroglucan gums, gum arabic, alginates, pectins, polyoses, guar gums, locust bean gum, linseed gums, dextrans, pectins, amylose, amylopectin, dextrins, gelatins, casein, methyl cellulose, carboxymethyl cellulose, and hydroxyethyl cellulose,
    wherein preparation (A)—based on the weight thereof—comprises,
    a1) 0.01 to 1 wt. % keratin hydrolysate(s) having molar masses from 400 to 1200 dalton and obtained from the cortex and/or cuticle of keratinic fibers, and
    a2) 0.01 to 5 wt. % dimethicone,
    with the proviso that preparation (A)—based on the weight thereof—comprises 0.1 to 6 wt. % compound(s) from groups a1) and a2).

2. The agent according to claim 1, wherein preparation (A) comprises 0.05 to 0.75 wt. % keratin hydrolysate(s).

3. The agent according to claim 1, wherein preparation (A) comprises 0.1 to 0.5 wt. % wt. % keratin hydrolysate(s).

4. The agent according to claim 1, wherein preparation (A) comprises 0.05 to 4 wt. % Dimethicone.

5. The agent according to claim 1, wherein preparation (A) comprises 0.1 to 2.5 wt. % Dimethicone.

6. The agent according to claim 1, wherein preparation (A) comprises persulfate salts in a quantity of 20 to 45 wt % based on the total weight of the respective agent.

7. The agent according to claim 1, wherein preparation (B) has a pH value of 3 to 5.

8. The agent according to claim 1, wherein preparation (B) has a viscosity from 1,000 mPa·s to 50,000 mPa·s during measurements in a rotational viscometer from Brookfield, spindle size 4, at 25° C. and 4 rpm.

9. The agent according to claim 1, wherein preparation (A) and preparation (B), wherein combined together, form a completely mixed and ready-to-use agent having a viscosity from 10,000 mPa·s to 50,000 mPa·s during measurements in a rotational viscometer from Brookfield, spindle size 5, at 25° C. and 4 rpm.

10. The agent according to claim 9, wherein the completely mixed and ready-to-use agents have a pH value between 9 and 12.

11. A method for changing the color of keratinic fibers, comprising applying the agent according to claim 1 to the keratinic fibers, and rinsing off the keratinic fibers.

* * * * *